United States Patent
Hansen et al.

(10) Patent No.: US 10,122,222 B2
(45) Date of Patent: *Nov. 6, 2018

(54) MAGNETIC POWER TRANSMISSION UTILIZING PHASED TRANSMITTER COIL ARRAYS AND PHASED RECEIVER COIL ARRAYS

(71) Applicant: TC1 LLC, St. Paul, MN (US)

(72) Inventors: John Freddy Hansen, Pleasanton, CA (US); Ethan Petersen, Pleasanton, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/717,271

(22) Filed: Sep. 27, 2017

(65) Prior Publication Data

US 2018/0040418 A1 Feb. 8, 2018

Related U.S. Application Data

(62) Division of application No. 13/953,629, filed on Jul. 29, 2013, now Pat. No. 9,805,863.

(60) Provisional application No. 61/676,723, filed on Jul. 27, 2012, provisional application No. 61/790,795, filed on Mar. 15, 2013, provisional application No. 61/676,656, filed on Jul. 27, 2012.

(51) Int. Cl.
*H02J 50/80* (2016.01)
*A61N 1/378* (2006.01)
*A61N 1/372* (2006.01)
*H01F 38/14* (2006.01)
*H02J 50/12* (2016.01)
*H02J 50/40* (2016.01)

(52) U.S. Cl.
CPC ............ *H02J 50/80* (2016.02); *A61N 1/3787* (2013.01); *A61N 1/37229* (2013.01); *H01F 38/14* (2013.01); *H02J 50/12* (2016.02); *H02J 50/40* (2016.02)

(58) Field of Classification Search
CPC ............... H02J 5/005; H02J 7/25; H02J 17/00
See application file for complete search history.

(56) References Cited

U.S. PATENT DOCUMENTS

| | | | | |
|---|---|---|---|---|
| 6,650,213 B1 * | 11/2003 | Sakurai | ............... | G06K 7/0008 335/296 |
| 2009/0112291 A1 * | 4/2009 | Wahlstrand | .......... | A61N 1/3787 607/61 |
| 2010/0033021 A1 * | 2/2010 | Bennett | ................... | H02J 17/00 307/104 |

(Continued)

*Primary Examiner* — Rexford Barnie
*Assistant Examiner* — David Shiao
(74) *Attorney, Agent, or Firm* — Armstrong Teasdale LLP

(57) ABSTRACT

An improved wireless transmission system for transferring power over a distance. The system includes a transmitter generating a magnetic field and a receiver for inducing a voltage in response to the magnetic field. In some embodiments, the transmitter can include a plurality of transmitter resonators configured to transmit wireless power to the receiver. The transmitter resonators can be disposed on a flexible substrate adapted to conform to a patient. In one embodiment, the polarities of magnetic flux received by the receiver can be measured and communicated to the transmitter, which can adjust polarities of the transmitter resonators to optimize power transfer. Methods of use are also provided.

20 Claims, 10 Drawing Sheets

(56) References Cited

U.S. PATENT DOCUMENTS

| | | | |
|---|---|---|---|
| 2010/0314946 A1* | 12/2010 | Budde | H02J 5/005 307/104 |
| 2012/0007437 A1* | 1/2012 | Fells | H01F 38/14 307/104 |
| 2012/0158407 A1* | 6/2012 | Forsell | A61B 5/0028 704/275 |
| 2012/0169139 A1* | 7/2012 | Kudo | H02J 5/005 307/104 |
| 2013/0119773 A1* | 5/2013 | Davis | H02J 5/005 307/104 |
| 2013/0149960 A1* | 6/2013 | Dec | H04B 5/0081 455/41.1 |
| 2013/0241302 A1* | 9/2013 | Miyamoto | H02J 50/12 307/104 |

* cited by examiner $$k \approx \frac{A_2}{A_1} \cos\Theta$$

MAGNETIC POWER TRANSMISSION UTILIZING PHASED TRANSMITTER COIL ARRAYS AND PHASED RECEIVER COIL ARRAYS

CROSS-REFERENCE TO RELATED APPLICATIONS

This application is a divisional of U.S. application Ser. No. 13/953,629, filed on Jul. 29, 2013, titled "Magnetic Power Transmission Utilizing Phased Transmitter Coil Arrays and Phased Receiver Coil Arrays", which claims the benefit of U.S. Provisional Application No. 61/676,723, filed on Jul. 27, 2012, titled "Magnetic Power Transmission Utilizing Phased Transmitter Coil Arrays and Phased Receiver Coil Arrays", U.S. Provisional Application No. 61/790,795, filed on Mar. 15, 2013, titled "Magnetic Power Transmission Utilizing Phased Transmitter Coil Arrays and Phased Receiver Coil Arrays", and U.S. Provisional Application No. 61/676,656, filed on Jul. 27, 2012, titled "Resonant Power Transmission Coils and Systems".

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to methods and apparatus for transmitting and receiving power wirelessly, and in various respects, mechanical circulatory support.

BACKGROUND

Powered devices need to have a mechanism to supply power to the operative parts. Typically systems use a physical power cable to transfer energy over a distance. There has been a continuing need for systems that can transmit power efficiently over a distance without physical structures bridging the physical gap.

Systems and methods that supply power without electrical wiring are sometimes referred to as wireless energy transmission (WET). Wireless energy transmission greatly expands the types of applications for electrically powered devices. One such example is the field of implantable medical devices. Implantable medical devices typically require an internal power source able to supply adequate power for the reasonable lifetime of the device or an electrical cable that traverses the skin. Typically an internal power source (e.g., battery) is feasibly for only low power devices like sensors. Likewise, a transcutaneous power cable significantly affects quality of life (QoL), infection risk, and product life, among many drawbacks.

More recently there has been an emphasis on systems that supply power to an implanted device without using transcutaneous wiring. This is sometimes referred to as a Transcutaneous Energy Transfer System (TETS). Frequently energy transfer is accomplished using two magnetically coupled coils set up like a transformer so power is transferred magnetically across the skin. Conventional systems are relatively sensitive to variations in position and alignment of the coils. In order to provide constant and adequate power, the two coils need to be physically close together and well aligned.

Existing systems that transmit power wirelessly based on magnetic fields typically operate either in the near-field only, where the separation of the transmitter and receiver coils is less than the dimension of the coils, or in mid-range, where the separation is comparable to the coil dimensions, but then only with single a transmitter and a single receiver coil. Single-transmitter-coil, single-receiver-coil systems are susceptible to a loss in power transmission if the receiver coil is oriented such that no magnetic fields lines emanating from the transmitter coil passes through the receiver coil, e.g., if a flat receiver coil is oriented with its normal perpendicular to the magnetic field lines.

SUMMARY OF THE DISCLOSURE

A wireless power transfer system is provided, comprising a flexible substrate adapted to conform to the body of a patient, a first transmitter resonator disposed on the flexible substrate, a second transmitter resonator disposed on the flexible substrate, the second transmitter resonator being in electronic communication with the first transmitter resonator; a receiver resonator; and a transmit controller configured to drive the first and second transmitter resonators to deliver wireless energy to the receiver resonator.

In some embodiments, the flexible substrate comprises a flexible fabric. In other embodiments, the flexible substrate is a material selected from the group consisting of Kapton, a polymide film, a polyester film, a cloth, and a rubber.

In one embodiment, the flexible substrate is covered with a padding to better match a contour of the body.

In some embodiments, the second transmitter resonator is driven out-of-phase from the first transmitter resonator.

In one embodiment, the first and second resonators coils are substantially rigid.

In some embodiments, the transmit controller is configured to operate in a test mode to drive the first transmitter resonator individually while a receive controller in the receiver resonator is configured to record a polarity of the magnetic flux received from the first transmitter resonator.

In another embodiment, the transmit controller is further configured to drive the second transmitter resonator individually while the receive controller in the receiver resonator is configured to record a polarity of the magnetic flux received from the second transmitter resonator.

In some embodiments, the receive controller is configured to communicate the measured polarity of the magnetic flux received from the first transmitter resonator to the transmit controller, and the transmit controller is configured to adjust transmission of power from the first transmitter resonator based on the recorded polarity.

In one embodiment, the receive controller is configured to communicate the measured polarity of the magnetic flux received from the second transmitter resonator to the transmit controller, and the transmit controller is configured to adjust transmission of power from the second transmitter resonator based on the measured polarity.

A method of adjusting wireless power transmission in a TET system is provided, comprising the steps of transmitting power from a first transmitter resonator external to a patient to a receiver resonator implanted within the patient, measuring a first polarity of magnetic flux received by the receiver resonator, transmitting power from a second transmitter resonator external to the patient to the receiver resonator implanted within the patient, measuring a second polarity of magnetic flux received by the receiver resonator, communicating the measured first and second polarities from the receiver resonator to a controller of the first and second transmitter resonators; and adjusting transmission of power from the first and second transmitter resonators based on the measured first and second polarities.

In some embodiments, the adjusting step comprises reversing a polarity of the first transmitter resonator.

In other embodiments, the adjusting step comprises reversing a polarity of the second transmitter resonator.

In some embodiments, the adjusting step comprises turning off the first transmitter resonator.

In one embodiment, the adjusting step comprises turning off the second transmitter resonator.

In some embodiments, the adjusting step comprises adjusting a polarity of one or more of the first and second transmitter resonators to maximize power received by the receiver resonator.

A wireless power transmitter is also provided, comprising coil circuitry including at least two transmit resonators, and driver circuitry including a voltage source, the driver circuitry configured to excite the coil circuitry to transmit wireless power from the at least two transmit resonators to a receiver.

In one embodiment, the coil circuitry includes four transmit resonators.

In another embodiment, the at least two transmit resonators comprise four resonators arranged in a 2×2 array.

In some embodiments, the transmit resonators are operated out of phase.

In other embodiments, the transmit resonators are operated in phase.

In one embodiment, at least one of the transmit resonators is operated in phase and at least one of the transmit resonators is operated out of phase.

A wireless power transfer system is provided, comprising first and second transmitter resonators configured to transmit wireless power to a receiver resonator implanted within a patient, a receive controller configured to measuring first and second polarities of magnetic flux received by the receiver resonator from the first and second transmitter resonators, respectively, the receive controller configured to communicate the measured first and second polarities to a transmit controller of the first and second transmitter resonators, the transmit controller configured to adjust transmission of power from the first and second transmitter resonators to the receiver resonator based on the measured first and second polarities to maximize power transfer.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
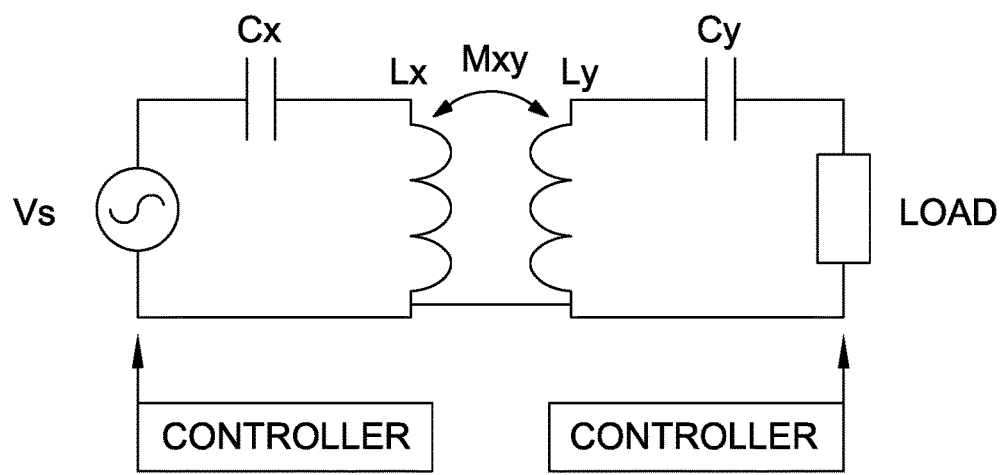
FIG. 1 illustrates a basic wireless power transfer system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the invention are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, at least 0.05, at least 0.1, or at least 0.15.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Turning now to FIG. 1, a simplified circuit for wireless energy transmission is shown. The exemplary system shows a series connection, but the system can be connected as either series or parallel on either the transmitter or receiver side.

The exemplary transmitter includes a coil $L_x$ connected to a power source $V_s$ by a capacitor $C_x$. The exemplary receiver includes a coil $L_y$ connected to a load by a capacitor $C_y$. Capacitor $C_x$ may be configured to make $L_x$ resonate at a desired frequency. Capacitance $C_x$ of the transmitter coil may be defined by its geometry. Inductors $L_x$ and $L_y$ are connected by coupling coefficient k. $M_{xy}$ is the mutual inductance between the two coils. The mutual inductance, Mxy, is related to coupling coefficient, k.

$$Mxy = k\sqrt{Lx \cdot Ly}$$

In the exemplary system a power source Vs can be in series with a transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (as shown in FIG. 1) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency, f, is 250 kHz. Then, for each cycle the load removes a certain amount of energy from the resonance:

$$e_L = \frac{P_L}{f} = 60 \,\mu\text{J} \quad \text{Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self inductance of the receiver coil was found to be 60 uH. From the energy and the inductance, the voltage and current in the resonator could be calculated.

$$e_y = \frac{1}{2} L i^2$$

$$i_y = \sqrt{\frac{2e_y}{L}} = 3.74 A \text{ peak}$$

$$v_y = \omega L_y i_y = 352 V \text{ peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \mu J}{0.05} = 8.4 mJ$$

For the same circuit the self inductance of the transmitter coil was 146 uH as mentioned above. This results in:

$$i_x = \sqrt{\frac{2e_x}{L}} = 10.7 A \text{ peak}$$

$$v_x = \omega L_x i_x = 2460 V \text{ peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
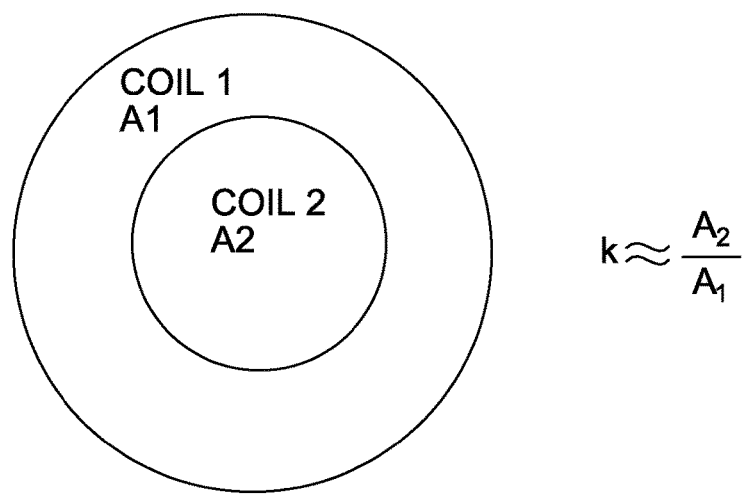
FIG. 2 illustrates the flux generated by a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
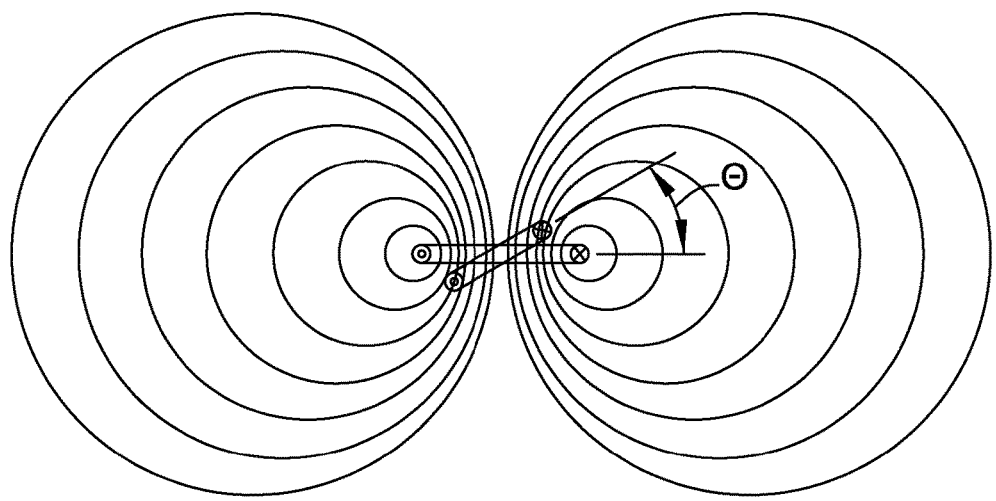
FIGS. 3A-3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

Figure 3B:
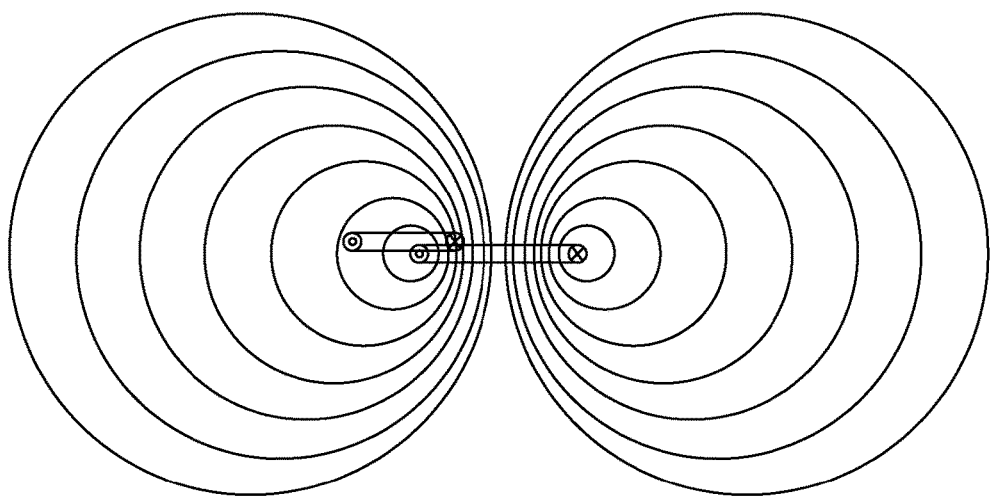

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

As described above, a typical TET system can be subdivided into two parts, the transmitter and the receiver. Control and tuning may or may not operate on the two parts independently. For example, as shown in FIG. 1, the transmitter or the receiver or both may include a controller. The goal of this invention is to minimize the effect of relative spatial position and orientation on the magnetic field power transfer rate between a transmitter and a receiver.

According to one embodiment, a TET system can include a set of transmitter coils and a set of receiver coils. The number of coils within each set can be as few as one, however, if there is only one receiver coil there must be at least two transmitter coils, and if there is only one transmitter coil there must be at least two receiver coils. Thus, at least one of the receiver or the transmitter must have more than one coil.

This invention modifies the existing components of a magnetic power transmission system, specifically it introduces phased arrays of transmitter coils and/or phased arrays of receiver coils. By utilizing information transmitted back from the receiver to the transmitter, the system can guarantee that a maximum magnetic flux reaches the receiver coils for a given geometry. This allows for more flexibility in the spatial arrangement between the transmitter and receiver by maintaining a more constant rate of power transfer than presently exists with existing systems. Various aspects of the invention are directed to grouping of a plurality of coils and structures and methods for driving and/or controlling the coils.

Figure 4:
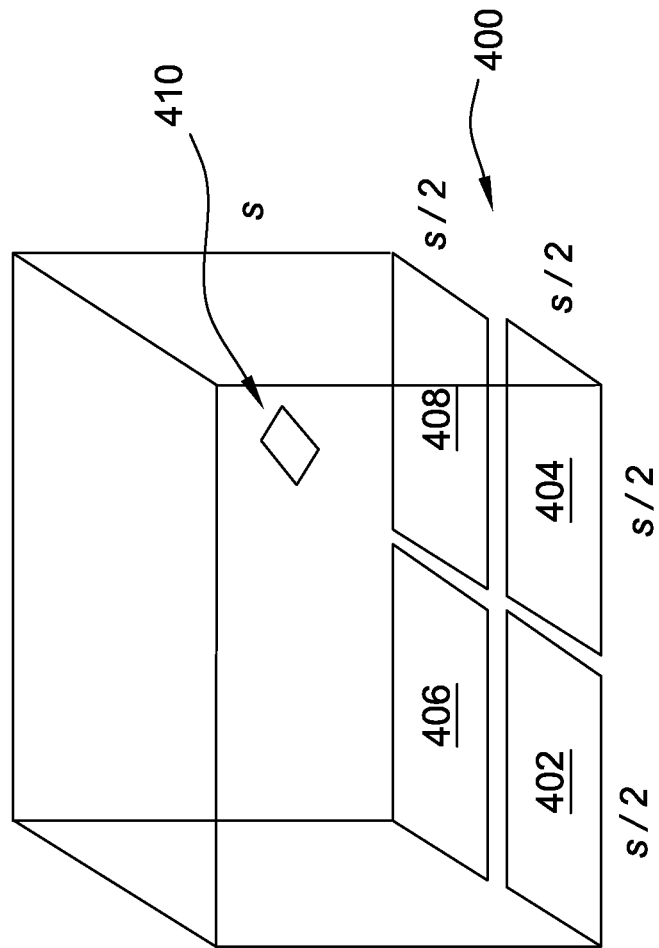
FIG. 4 illustrates a resonator with multiple coils.

FIG. 4 shows an example of a transmitter 400 of a TET system with multiple transmit coils 402, 404, 406, and 408. The transmit coils can be equally sized and placed, for example, in the square arrangement shown in FIG. 4. Also shown in FIG. 4 is a receiver coil 410 placed adjacent to the transmit coils in a random position and orientation with respect to the transmit coils. As described above and referencing FIG. 1, each transmit coil can include an inductor Lx and can be connected to a power source Vs by a capacitor Cx. The receive coil can also include an inductor Ly connected to a load by a capacitor Cy. Capacitor Cx may be configured to make Lx resonate at a desired frequency.

The coils can be driven by independent, but synchronized, driver circuits, or they can be driven by a single common circuit, such as those described below. In some embodiments, pairs of transmit coils can be driven by a single circuit.

Figure 5A:
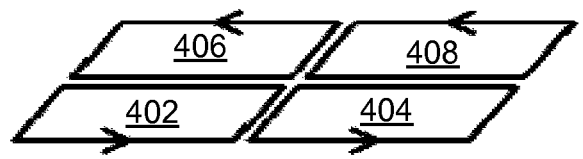
FIGS. 5A-5C illustrate various in-phase and out-of-phase orientations of multiple coil systems.
Figure 5B:
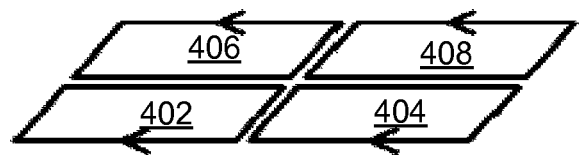
Figure 5C:
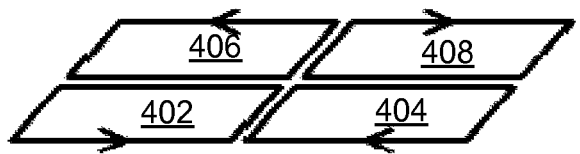

In one embodiment, shown in FIG. 5A, the transmit resonators 402, 404, 406, and 408 can be arranged "in phase", which has the equivalent effect of a large single coil. In a second embodiment, shown in FIG. 5B, two of the resonators can be arranged out-of-phase (first symmetry axis) with respect to the remaining two coils. In a third embodiment, shown in FIG. 5C, two of the coils are out-of-phase (second symmetry axis) with respect to the remaining two coils.

Figure 6:
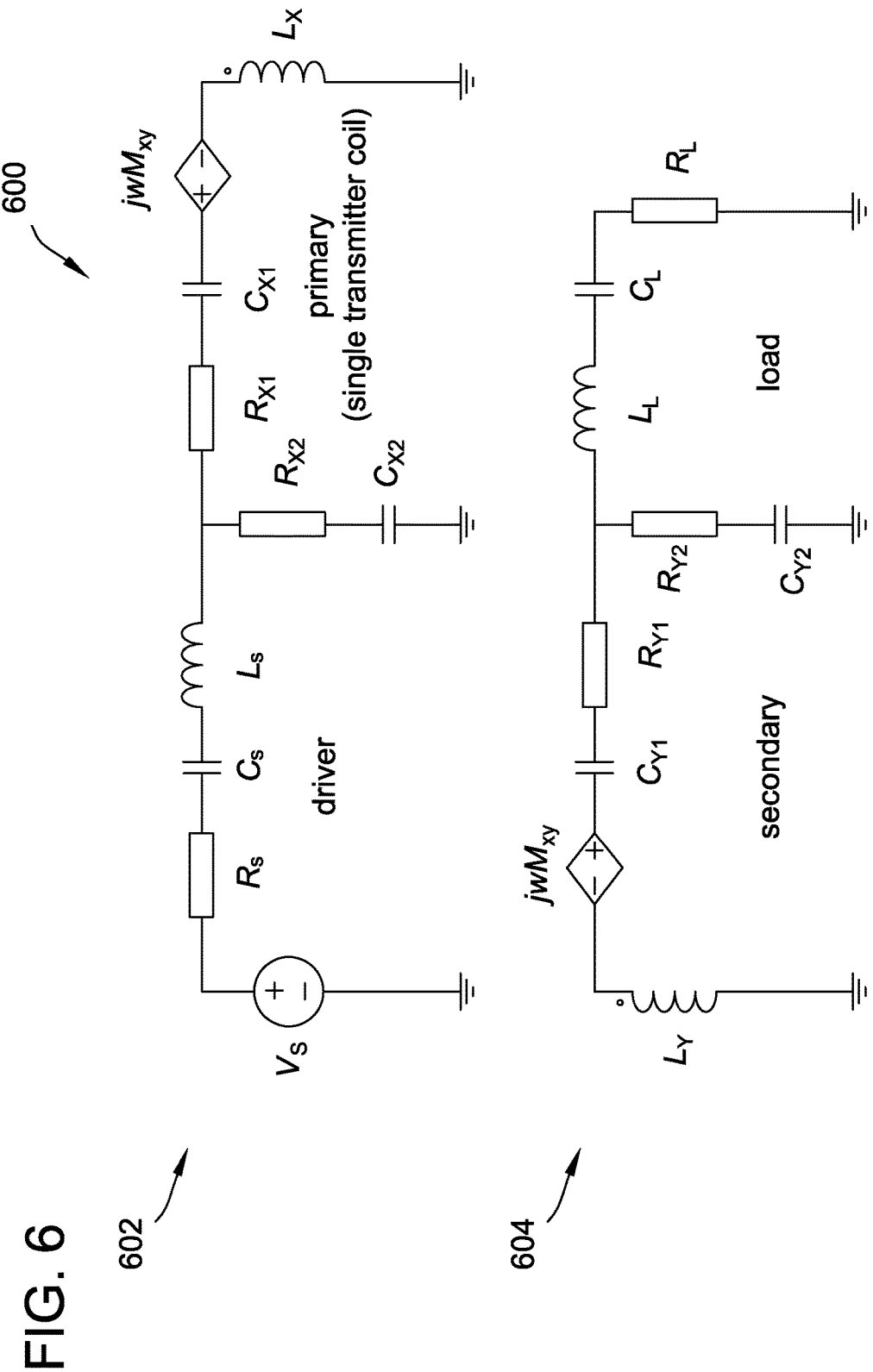
FIG. 6 illustrates circuitry for a single coil transmitter and single core receiver.

Multiple transmitter coil control systems can be based on a single transmitter circuit. FIG. 6 illustrates a basic TET system 600, including a transmitter 602 and a receiver 604. The transmitter 602 can include a voltage source $V_S$, which can be a variable voltage, fixed or variable frequency voltage source. A driver circuit of the transmitter 602 can include a resistor $R_S$, a capacitor $C_S$ (optional) and an inductor $L_S$. The single transmitter coil or resonator $L_X$ of transmitter 602 can comprise a pair of resistors $R_{X1}$ and $R_{X2}$, a pair of capacitors $C_{X1}$ and $C_{X2}$, and an inductor $L_X$. Capacitor $C_{X2}$ can be variable to compensate for changes in mutual inductance, $M_{XY}$, between the transmitter and the receiver. The driver circuit can be configured to excite the primary or single transmitter coil. The receiver 604 can include a receiver coil having a pair of resistors $R_{Y1}$ and $R_{Y2}$, a pair of capacitors $C_{Y1}$ and $C_{Y2}$, and an inductor $L_Y$. The load of the receiver can comprise a resistor $R_L$, a capacitor $C_L$, and an inductor $L_L$. In some embodiments, capacitor $C_{Y2}$ can be variable to compensate for changes in $M_{XY}$. The mutual inductance $j\omega M_{XY}$ between $L_X$ and $L_Y$ is shown in both transmitter 602 and receiver 604 of FIG. 6.

Figure 7:
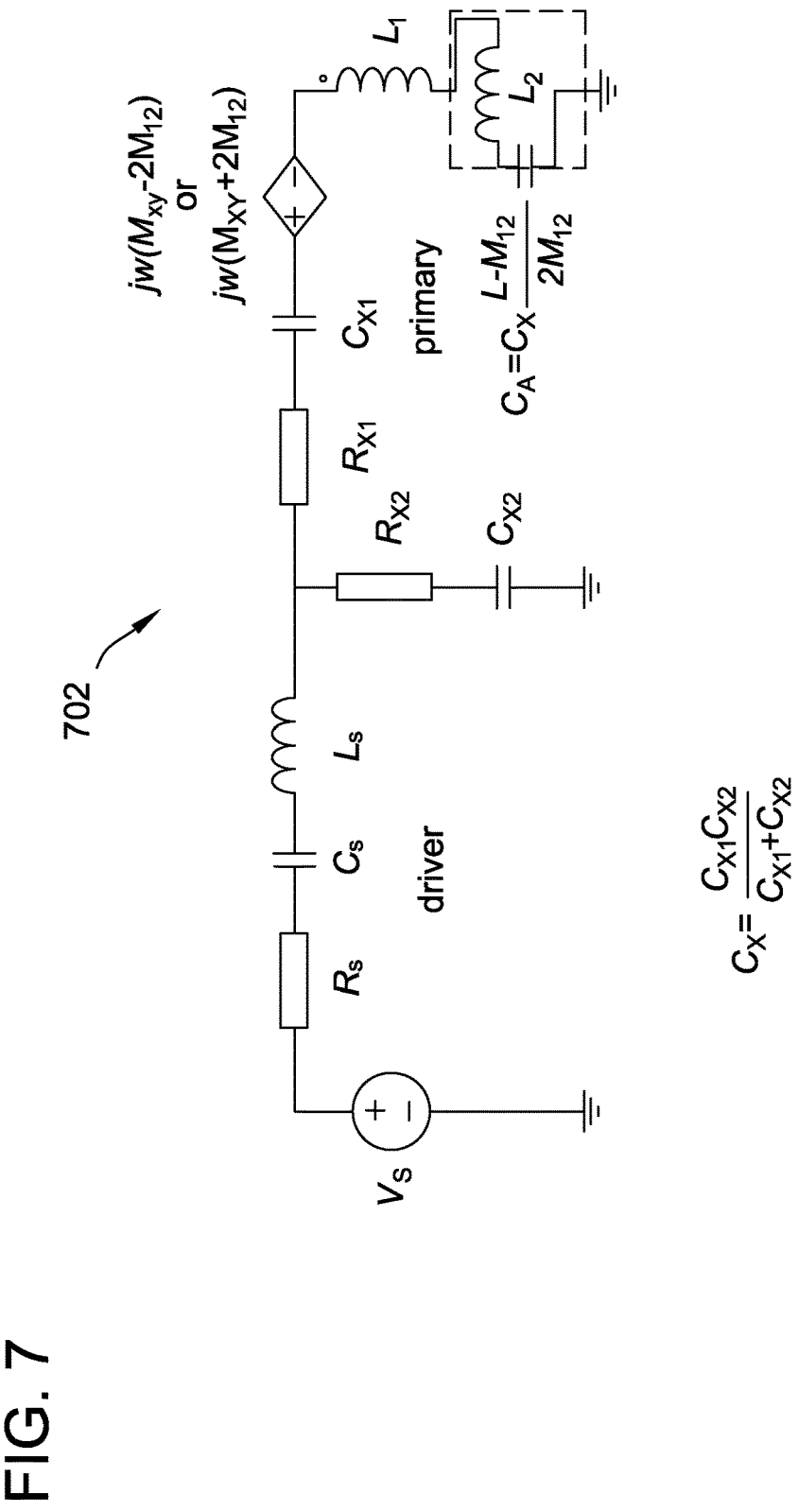
FIG. 7 illustrates circuitry for a dual coil transmitter.

FIG. 7 illustrates a transmitter 702 in which the transmitter includes two transmit resonators $L_1$ and $L_2$. As shown, this circuit is a modification of the circuit described above in FIG. 6 which has only a single transmit coil. Transmitter 702 includes many of the same components described above, including voltage source $V_S$, resistors $R_S$, $R_{X1}$, and $R_{X2}$, capacitors $C_S$, $C_{X1}$, and $C_{X2}$, inductors $L_S$ and $L_1$. Additionally, the transmitter can include a second transmit coil, inductor $L_2$. As described above, the transmitter can comprise driver circuitry, as shown, configured to excite the primary circuitry including the transmit coils. In embodiments where the coils are operated out of phase, an additional capacitor $C_A$ can be coupled to the inductor $L_2$, as shown. This additional capacitor can function to reduce primary capacitance when the coils operate out of phase. When the transmitter resonators operate in phase, the mutual inductance between the transmitter and receiver can be represented as $j\omega(M_{XY}-2M_{12})$. When the transmitter resonators operate out of phase, the mutual inductance between the transmitter and the receiver can be represented as $j\omega(M_{XY}+2M_{12})$.

Without $C_A$, the circuit compensation would have to be done entirely by the variable capacitance $C_{X2}$, requiring a much larger variable range of $C_{X2}$. A larger range of $C_{X2}$ is disadvantageous because of increased cost, more difficult circuit control, and lower precision in the circuit compensation that in turn leads to an overall lower power transfer efficiency.

With multiple transmitter coils there is a mutual inductance not only between each transmitter coil and the receiver coil, but between each pair of transmitter coils. With two transmitter coils, we can call the latter $M_{12}$. Switching phase on a transmitter coil causes a sign change on the $M_{12}$-induced voltage. This is equivalent of thinking of both transmitter coils as a system with a single self-inductance, and saying that the self-inductance is changed. As a result, the primary circuit capacitance has to be adjusted, or else the eigen frequency LC may be wrong.

Figure 8:
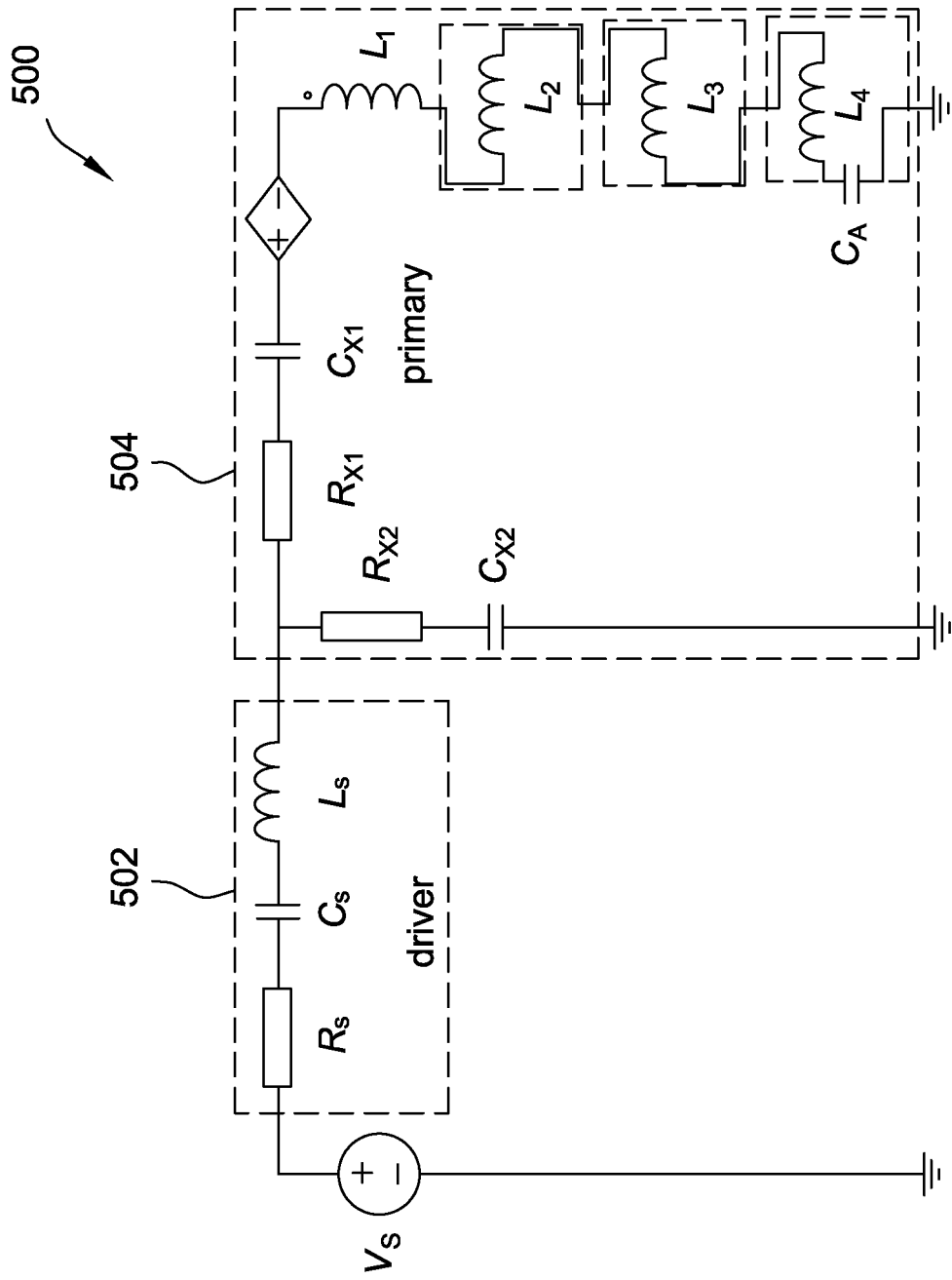
FIG. 8 illustrates circuitry for a quad coil transmitter.

FIG. 8 illustrates an example of a transmitter 500 having four transmit coils or resonators, $L_1$, $L_2$, $L_3$, and $L_4$. The transmitter can also include controller circuitry (not shown), as shown and described above in FIG. 1. Although this specific embodiment is illustrated with four transmit coils, it should be understood that any number of resonators can be implemented using the same principles. The transmitter 500 can include at least one voltage source $V_S$, which can be a variable voltage, fixed or variable frequency voltage source. A driver circuit 502 of the transmitter can include a resistor $R_S$, a capacitor $C_S$ (optional) and an inductor $L_S$. A primary circuit 504 of the transmitter having four transmitter resonators can comprise a pair of resistors $R_{X1}$ and $R_{X2}$, a pair of capacitors $C_{X1}$ and $C_{X2}$, an optional capacitor $C_A$, and four inductors $L_1$, $L_2$, $L_3$, and $L_4$. The driver circuit can be configured to excite the primary transmitter coil. As described above, the transmitter can comprise driver circuitry, as shown, configured to excite the primary circuitry including the transmit coils.

If all four coils are placed symmetrically, only a single capacitor $C_A$ is required to compensate for mutual inductance changes when operating all coils in-phase or pair-wise out of phase. In this embodiment, the transmitter system provides efficient power transfer without a significant increase in complexity. Moreover, the number of system options is increased significantly.

One will appreciate from the description herein that the coils can be modified in a number of ways—number, position, and phase—to achieve a desired outcome. The system also provides a simple way to control the multiple transmission coils to achieve a greater number of possibilities. In some embodiments, multiple coil systems can comprise two coils placed in the same plane, four coils placed in a square array in the same plane, two coils at a 90 degree angle to each other, four coils arranged in pairs, with each pair at an angle to each other. Additionally, coils can be placed at angles of up to 120, 135, 150, etc degrees to each other. In another embodiment, a large coil can circumscribe a smaller coil in the same plane. In another embodiment, coils of the same or different size and same plane can be offset along an axis. In one embodiment, pairs of coils can have the same size and same normal vector, but offset along the axis and one pair rotated 90 degrees around the axis. Additionally, in one embodiment there can be 2 four coil arrays of the same size and orientation, but offset along an axis.

The advantage of a multi-transmitter coil system is that the receiver can be located anywhere, and in any orientation, in the volume adjacent to either of the transmission coils. The use of a large transmission coil is both costly and cumbersome compared to the multiple smaller coils. The inventive system is also believed to be effective in a wider range of situations, in part because the phases can be modified.

A TET system according to one embodiment can operate in two modes: a test mode and a power transmission mode. In its simplest configuration (see other configuration options below), there are several transmitter coils, but typically only one receiver coil.

Generally speaking, in the test mode, the transmitter system (such as the transmitter of FIGS. 4-5) can operate one transmission resonator at a time, while the receiver measures the polarity (and optionally the amplitude and/or phase, see below) of the received magnetic flux. The receiver can measure the polarity and, optionally, the amplitude of the magnetic flux, with a controller or processor and additional sense and signal processing circuitry located within the receiver. This information can be transmitted back to the transmitter controller. The information measured or recorded by the receiver can then be processed and transmitted back to the transmitter controller. Communication between the receiver and transmitter can be, for example, on a separate communications channel (not shown) or by transmitter modulation. This information can be telemetered by the same magnetic field coils, or by any other wireless technique, such as radio, including BlueTooth, WiFi, etc.

It is assumed the wavelength of the magnetic field is much larger than the characteristic dimensions of the transmitter and the receiver. If this is not the case, the receiver needs to record phase information during the test mode, and each transmitter coil should be offset by its phase lag during power transmission mode. In applications where the operating frequency is hundreds of kilohertz (e.g., 250 kHz), the wavelength is at least hundreds of meter (1.2 km at 250 kHz), so for devices no larger than a few meters, phase information is unnecessary and coils should operate either in phase (0° phase) or out-of-phase (180° phase), as described.

Since power transmission in a TET system typically occurs at frequencies of hundreds of kilohertz, the test mode can be completed on the order of a few milliseconds, or even than one millisecond, even for up to 100 separate transmitter coils, much faster than any realistic change of the geometry. This means the geometry of the transmitter can be tested regularly, e.g., once a second, with no significant loss in power transfer rate. It is also possible to configure the receiver to alert the transmitter if the power transfer rate drops, and then begin a new test mode.

In the power transmission mode, all transmission coils can operate simultaneously, but can be divided into groups based on the polarity (plus or minus) of the received magnetic flux from each coil in the test mode. Thus, transmission of power from the transmitter resonators to the receiver resonator can be adjusted based on the recorded polarities of each transmitter resonator from the test mode. The goal is to maximize the amount of flux passing through the receiver resonator. But, flux in the plus direction cancels out flux in the negative direction. As FIG. 3B illustrates, there can be flux passing through the bottom to the top of a receiver then pass again through the top to the bottom. This results in net zero energy. For an array of transmitter coils, they can have a "plus" or "minus" polarity. If a receiver intercepts a "plus" and "minus" from its bottom, the energy cancels out to a net zero. But if the receiver intercepts a "plus" from its top and a "minus" from its bottom, the energy adds up. In an environment where the implanted receiver can assume a random orientation relative to the external transmitter, which itself can be wrapped around the patient's body, mixing transmitter polarities allows for more net energy to accumulate in the receiver.

For example, in a four coil transmitter system as shown in FIGS. 4-5, the coils can be divided into two groups of two transmitter coils. In the first group, all coils are operating in phase with each other (i.e., the currents in all coils in this group are in phase). In the second group, all coils are operating out-of-phase with the coils in the first group.

In this configuration, the magnetic flux (and thus received electric power) is maximized given the geometry of the system.

There are several possible permutations of the test mode. Any binary search algorithm can be used, i.e., any number of transmitter coils could be powered at a time, as long as different combinations are tested in such a way as to deduce the appropriate polarity of each transmitter coil.

In one embodiment, to achieve maximum energy transfer the master transmitter controller can implement a process as follows (this is the binary algorithm):

1. The controller turns on each individual transmitter, one at a time, for a specific amount of time. The controller then waits for the receiver to send back information relating to the power received by each transmitter coil. This process can be used to determine which, if any of the transmitter coils transferred any power.

2. Next, the master controller can turn on the transmitter coils that successfully transferred power to the receiver, both with the same polarity. The receiver can send back the amount of power received, and compare that to the power originally received by the individual coils.

3. If the power received was less than originally received in 1. above, the master controller can adjust the polarity of the individual transmitter coils. The receiver compares the amount of power received in each iteration to previously received power levels until a maximum power and ideal polarity configuration is identified.

The difference between this invention and existing solutions is that this invention guarantees the avoidance of zero power transfer situations, and it significantly improves the power transfer rate in situations where other solutions can only provide a marginal power transfer rate. It can be cheaper to manufacture than exotically shaped receiver coils. The disadvantages may be that the mass of the transmitter increases, which means that there is a trade-off between mass and the power transfer improvements offered by this system when the transmitter is carried by a person. Another potential disadvantage is that some more control logic is needed by this system.

Utilizing an array of transmitter resonators allows for individually rigid resonators and electronics to be combined into a flexible array that may be worn by a person or made to conform to a surface. In this manner, the coupling coefficient between the transmitting array and the receiver resonator can be tailored by turning on, turning off, or reversing the polarity of current through the transmitting coils. This allows increased power transfer efficiency. Various arrays of flexibly connected rigid coils are shown in FIGS. 9A-9C.

Figure 9A:
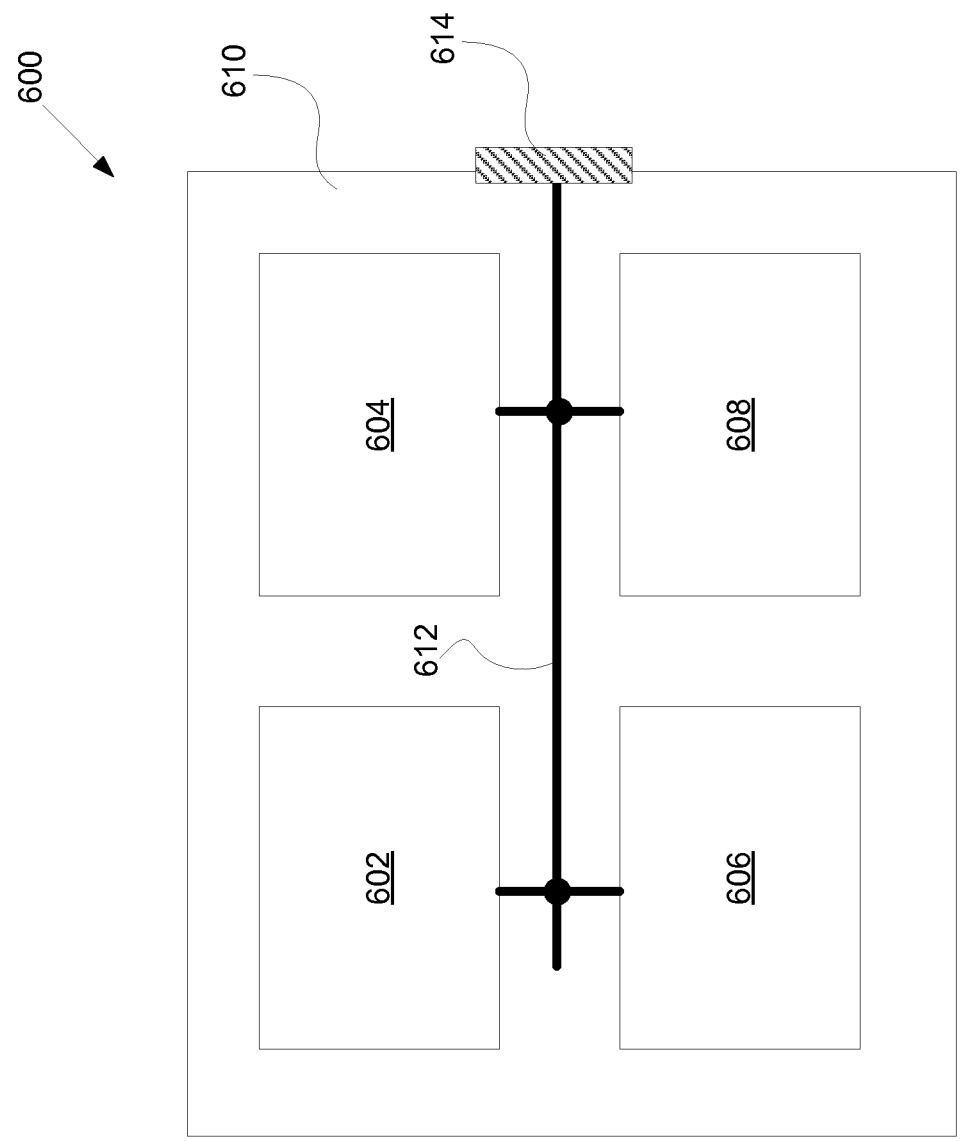
FIGS. 9A-9C illustrate a resonator with multiple flexibly connected rigid coils.

FIG. 9A shows one embodiment of a transmitter 600 with four distinct coil resonators, 602, 604, 606, and 608. In this embodiment, the coils can be mounted onto a flexible fabric or substrate 610 (flexible substrate shown). In some embodiments, the flexible substrate can comprise Kapton or other polymide films, polyester films, or cloth, such as cotton cloth. The individual resonators can be mounted to the flexible substrate or fabric and can be interconnected using a flexible circuit or discrete cabling 612 to allow communications between the resonators. The resonator can also include a connector 614 to an external power supply, for example. The transmit resonator can include or be connected to all the other electrical components and circuitry described above for operation in a TET system, including a controller, signal generator, power source, etc.

As shown in FIG. 9A, the coils are each connected to every other coil with cabling 612, but it should be understood that the specific connection patterns can vary (e.g., connecting the coils in series). As the flexible array conforms to a person's body or to an object used by the person, the array utilizes an algorithm running on a controller, as mentioned elsewhere in this disclosure, to determine an optimal arrangement of coil polarities to maximize the power transfer or power transfer efficiency to a separate receiver resonator.

Figure 9B:
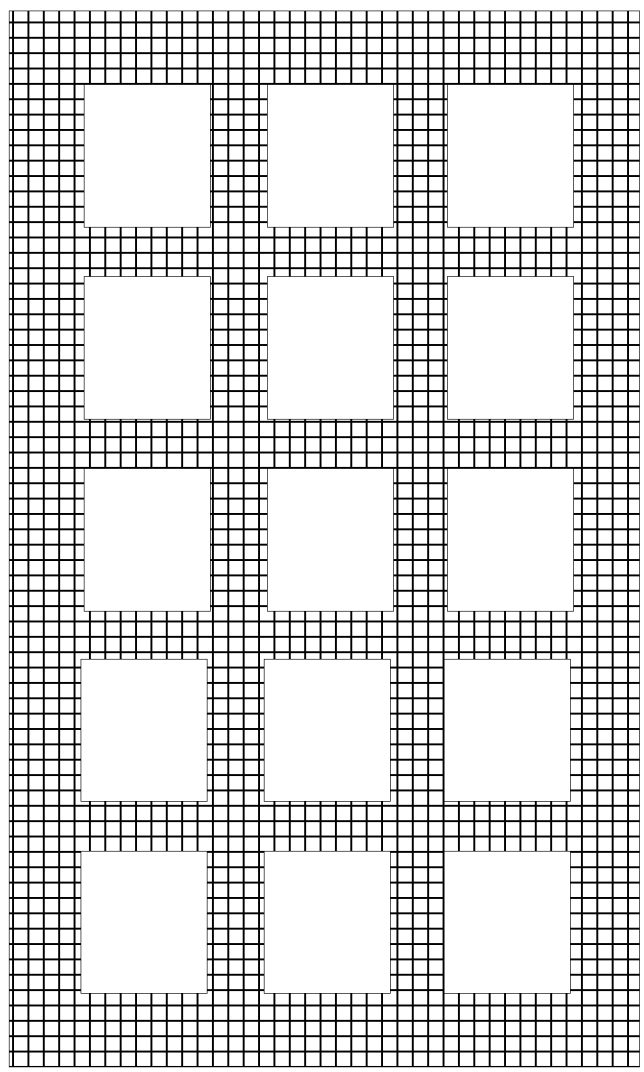
Figure 9C:
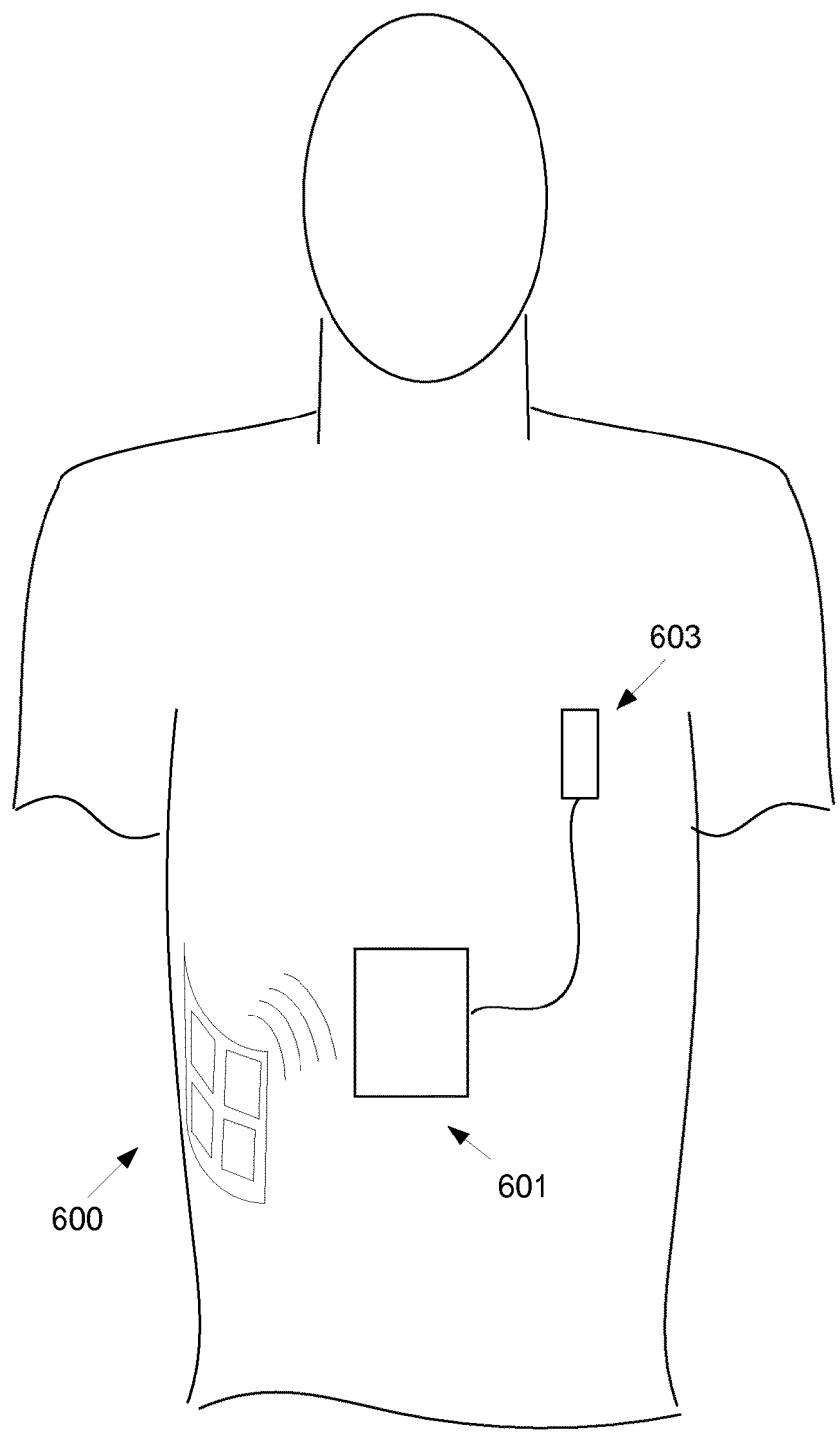

FIG. 9B illustrates another embodiment of a transmitter 600 with multiple rigid flexibly-connected coils. This particular embodiment can comprise a 50 cm by 30 cm resonator made using 15 individual 10 cm by 10 cm resonators. Each 10 cm by 10 cm resonator can be constructed on a rigid surface, minimizing the wear and degradation of the wire coil and resonator electronics, but can be mounted on a flexible substrate or fabric (flexible fabric shown). As in the embodiment of FIG. 9A, the individual resonators can be connected to each other with cabling or flexible circuitry.

FIG. 9C illustrates the transmitter 600 of FIG. 9A (or alternatively, of FIG. 9B) conformably mounted to the body of a human patient. As shown in FIG. 9C, the flexible substrate or fabric upon which multiple individual coils or resonators are mounted allows the resonator to conform to the body of the patient. In doing so, the transmit resonator can more effectively transmit wireless power or energy to a receiver 601 implanted within the body, which can be configured to deliver that power or energy to another implanted medical device, such as heart pump 603. The conformability of the resonator 600 allows the multiple coils or resonators to more efficiently transfer power to the implanted receiver 601 irrespective of the positioning or orientation of the receiver within the body. Since implanted devices can move or shift after implantation, the transmitter 600 of FIG. 9C advantageously compensates for shifts or movement of the implanted receiver.

When used in an environment with conductive metal surfaces, such as an operating theater or hospital, magnetic shielding can be utilized to minimize the parasitic losses of the transmitter array. Nearby moderately conductive objects comprised of steel, titanium, or similar materials act to both block the magnetic fields between the transmitter and receiver as well as dissipate the resonant energy as heat. Magnetic shielding such as ferrite can be used with the transmitter to minimize the effects of nearby parasitic objects, but materials such as ferrite are brittle. In one embodiment, a separate piece of ferrite can be placed on individual resonators only. This can allow for the array itself to remain flexible. Another approach is to use malleable magnetic metals in conjunction with insulator strips to provide both magnetic shielding and overall array flexibility.

Multiple coil systems according to this disclosure advantageously shape the magnetic field to maximize the power transmitted to the receiver. The shaping is accomplished with coils of any shape, including simple, flat coils that are grouped to operate either in-phase or out-of-phase with each other. This approach provides increased efficiency and reliability in situations where the receiver is not guaranteed to be stationary with respect to the transmitter, particularly in medically implanted wireless power transfer systems.

These techniques have not been contemplated by others in the art since many wireless power transfer systems to date have required chargers for objects such as cellular phones, consumer electronics, vehicles, etc, that remain stationary while charging. By contrast, for an implantable medical application, a patient must be free to move around even while the implanted device is receiving power.

As described above, the magnetic flux in the receiver coil can be maximized given the geometry of the system at the moment in time of the test mode. If the geometry of the system is changing with time, e.g., if the receiver is moving or rotating with respect to the transmitter (such as a person with an implanted receiver moving around in a bed with a transmitter below the mattress, or moving around a room or office with a wall transmitter), or if the transmitter coils are moving with respect to each other (such as a person with an implanted receiver who wears a garment with transmitters, and this garment is worn slightly differently at different times, or if the garment moves in the wind), the system can run the test mode again, to determine a new optimum grouping of the transmission coils.

As an optional feature, the receiver can record the amplitude of received magnetic flux (or received current, voltage, or power) during the test mode. This can be done in a situation where the system is not maximizing the received magnetic flux, but rather maximizes the power transfer ratio, i.e., in situations where power loss in the transmitter is an issue, such as when the transmitter is battery-powered instead of connected to wall power. By recording received magnetic flux amplitude, the system can choose to not power certain transmission coils in the power transmission mode, namely all those coils which did not produce a threshold value of magnetic flux in the test mode. A higher threshold value means a more power efficient system. A lower threshold value means more total power transmitted (down to zero threshold value, which maximizes the power transmitted as described above).

Note that the system could use, instead of just one receiver coil and an array of transmitter coils, two or more receiver coils along with one or more transmitter coils. In this case, during the test mode, each transmitter coil can be operated one at a time, while each receiver coil is operated one at a time, until all combinations are tested, and amplitude responses are recorded. Alternatively, any binary search algorithm can be used. Then, the best receiver coil (the coil with the largest sum total of magnetic flux received) can be selected for operation, and the transmitter coils grouped in-phase and out-of-phase as described above. Finally, the other receiver coils are connected in phase with the first receiver coil (such that all receiver coils contribute current to the receiver circuit in phase with each other). Just like what was described above, individual transmitter or receiver coils can be removed from the circuits if threshold values are not achieved.

The embodiments described herein do not depend on any particular shape, size, position, or orientation of transmitter or receiver coils. Coils of different shapes and sizes are allowed, at arbitrary positions and orientations, including overlapping. The number of coils needed typically is at least three (one receiver coil, two transmitter coils, or vice versa), but there is no upper limit to the number of coils that can be included in the system.

This disclosure can pertain to any device that receives power wirelessly at a distance from the power source, including all types of electronics (cell phones, portable computers, PDAs, mobile games, remote controls, etc), electric cars, trains, and other vehicles, or any other device that uses electric power. The invention could be used to charge the batteries of any such device, or to power it directly. The invention does not rely on either the transmitter or receiver being in resonance, although it can take advantage of such systems.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A wireless power transmitter, comprising:
coil circuitry including at least two transmit resonators; and
driver circuitry including a voltage source, the driver circuitry configured to excite the coil circuitry to transmit wireless power from the at least two transmit resonators to a receiver, wherein the driver circuitry is configured to adjust the transmission of wireless power based on a magnetic flux polarity of magnetic flux received by the receiver from each of the at least two transmit resonators, the magnetic flux polarity recorded at the receiver and communicated to the wireless power transmitter, and wherein the magnetic flux polarity is defined by a direction in which magnetic flux passes through the receiver.

2. The transmitter of claim 1 wherein the coil circuitry includes four transmit resonators.

3. The transmitter of claim 2 wherein the four transmit resonators are arranged in a 2×2 array.

4. The transmitter of claim 1 wherein the transmit resonators are operated out of phase relative to one another.

5. The transmitter of claim 1 wherein the transmit resonators are operated in phase relative to one another.

6. The transmitter of claim 1 wherein at least first and second transmit resonators of the transmit resonators are operated in phase relative to one another, and wherein at least a third transmit resonator is operated out of phase relative to the first and second transmit resonators.

7. The transmitter of claim 1, wherein the at least two transmit resonators lie in the same plane.

8. The transmitter of claim 1, wherein the at least two transmit resonators are oriented orthogonal to one another.

9. The transmitter of claim 1, wherein the at least two transmit resonators comprise a first transmit resonator circumscribing a second transmit resonator.

10. The transmitter of claim 1, further comprising a capacitor coupled to the at least two transmit resonators to compensate for mutual inductance changes.

11. The transmitter of claim 1, wherein the at least two transmit resonators are disposed on a flexible substrate.

12. The transmitter of claim 11, wherein the flexible substrate comprises a flexible fabric.

13. A wireless power transfer system, comprising:
first and second transmitter resonators configured to transmit wireless power to a receiver resonator implanted within a patient;
a receive controller configured to measure first and second polarities of magnetic flux received by the receiver resonator from the first and second transmitter resonators, respectively, the first and second magnetic flux polarities defined by a direction in which the magnetic flux from the first and second transmitter resonators passes through the receiver resonator, the receive controller configured to communicate the measured first and second polarities to a transmit controller of the first and second transmitter resonators;
the transmit controller being configured to adjust transmission of power from the first and second transmitter resonators to the receiver resonator based on the measured first and second polarities to maximize power transfer.

14. The wireless power transfer system of claim 13, wherein the first and second transmitter resonators are operated out of phase relative to one another.

15. The wireless power transfer system of claim 13, wherein the first and second transmitter resonators are operated in phase relative to one another.

16. The wireless power transfer system of claim 13, wherein the first and second transmitter resonators lie in the same plane.

17. The wireless power transfer system of claim 13, wherein the first and second transmitter resonators are oriented orthogonal to one another.

18. The wireless power transfer system of claim 13, wherein the first and second transmitter resonators comprise a first transmitter resonator circumscribing a second transmitter resonator.

19. The wireless power transfer system of claim 13, further comprising a capacitor coupled to the first and second transmitter resonators to compensate for mutual inductance changes.

20. The wireless power transfer system of claim 13, wherein the first and second transmitter resonators are disposed on a flexible substrate.

* * * * *